US005679773A

United States Patent [19]

Holmes

[11] Patent Number: 5,679,773
[45] Date of Patent: Oct. 21, 1997

[54] REAGANTS AND METHODS FOR IMMOBILIZED POLYMER SYNTHESIS AND DISPLAY

[75] Inventor: Christopher P. Holmes, Sunnyvale, Calif.

[73] Assignee: Affymax Technologies N.V, Greenford, United Kingdom

[21] Appl. No.: 374,492

[22] Filed: Jan. 17, 1995

[51] Int. Cl.$^6$ .................................................. C07K 1/04
[52] U.S. Cl. .................. 530/334; 530/333; 530/345; 430/56; 430/270
[58] Field of Search ................... 530/333, 334, 530/335; 430/56, 270

[56] References Cited

U.S. PATENT DOCUMENTS

| 4,593,029 | 6/1986 | Venuti et al. | 514/267 |
|---|---|---|---|
| 4,728,502 | 3/1988 | Hamill | 422/116 |
| 5,143,854 | 9/1992 | Pirrung et al. | 436/518 |
| 5,288,514 | 2/1994 | Ellman | 427/2 |
| 5,424,186 | 6/1995 | Fodor | 435/6 |
| 5,482,719 | 1/1996 | Guillet | 429/486 |

FOREIGN PATENT DOCUMENTS

| 1 472 937 | 5/1977 | United Kingdom . |
|---|---|---|
| WO 90/00626 | 1/1990 | WIPO . |
| WO 90/15070 | 12/1990 | WIPO . |
| WO 92/10092 | 6/1992 | WIPO . |
| WO 93/10162 | 4/1993 | WIPO . |
| WO 93/10183 | 5/1993 | WIPO . |
| WO 95/04160 | 9/1995 | WIPO . |

OTHER PUBLICATIONS

Greene, T.W., et al., *Protective Groups in Organic Synthesis*, published 1991 by John Wiley (N.Y.), pp. 1–362, see pp. 27, 62, 88, 89, 315, 349, and 362.

Dugave, C., et al., "Synthesis of Activated Disulfide Adducts Containing a 4-Diazocyclohexa-2,5-dienone Precursor for Photoaffinity Labelling," *Tetrahedron Letters*, 35(51):9557–9560, (1994).

Rajasekharan Pillai, V.N., et al., "New, Easily Removable Poly(ethylene glycol) Supports for the Liquid-Phase Method of Peptide Synthesis," *J. Org. Chem.*, 45(26):5364–5370 (1980).

Jones, G.H., et al., "Inhibitors of Cyclic AMP Phosphodiesterase: 1. Analogs of cilostamide and anagrelide," *Chemical Abstracts*, 106(13):102224 (1987); *J. Medical Chemistry*, 30(2):295–303 (1987) see compounds: 105763-67-5, 105763-74-4, 105763-73-3 and 105763-76-6.

Surrey, A.R., et al., *J. Am. Chem. Soc.*, 80:3469–3471 (1958).

Nagakura, I., et al., *Heterocycles*, 3(6):453–457 (1975).

Rich, D.H., et al., *J. Am. Chem. Soc.*, 97:1575–1579 (1975).

Barany, G., et al., *J. Am. Chem. Soc.*, 107:4936–4942 (1985).

Wang, S.S., *J. Org. Chem.*, 41(20):3258–3261 (1976).

Bellof, D., et al., *Chimia*, 39(10):317–320 (1985).

Abraham, N.A., et al., *Tetrahedron Letters*, 32(5):577–580 (1991).

Cook, R.M., et al., *Tetrahedron Letters*, 35(37):6777–6780 (1994).

Merrifield, *J. Am. Chem. Soc.*, 85:2149–2154 (1963).

Geysen, et al., *J. Immun. Meth.*, 102:259–274 (1987).

Frank, et al., *Tetrahedron*, 44:6031–6040 (1988).

Fodor, et al., *Science*, 251:767–777 (1991).

Bush, et al., *Amer. J. Optometry Physiol. Optics*, 65(9):722–728 (1988).

Green, M., et al., *Adv. Protein Chem.*, 29:85–133 (1975).

Safar et al., Jun. 1994, 24th National Medicinal Chemistry Symposium, P206 Generation of Peptide–like libraries using amino acid–like subunits.

Yoo and Greenberg, 1995, *J. Org. Chem.*, 60:3358–3364 Synthesis of oligonucleotides containing 3–alkyl carboxylic acids using universal, photolabile solid phase synthesis supports.

Teague, 1996, Tetrahedron Leters, 37(32):5751–5754 Facile synthesis of a o–nitrobenzyl photolabile linker for combinatorial chemistry.

*Primary Examiner*—Cecilia J. Tsang
*Assistant Examiner*—David Lukton
*Attorney, Agent, or Firm*—William B. Kezer; Lauren L. Stevens

[57] ABSTRACT

Compounds and methods for solid phase synthesis of organic molecules including peptides, oligonucleotides, benzodiazepines, β-turn mimetics, and prostaglandins. The present invention provides new reagents in the form of linking groups and resins and substrates having attached linking groups which are useful in solid phase synthesis of high density arrays of organic molecules. The invention also provides methods which increase yields of various organic synthesis strategies.

11 Claims, 3 Drawing Sheets

REAGANTS AND METHODS FOR IMMOBILIZED POLYMER SYNTHESIS AND DISPLAY

BACKGROUND OF THE INVENTION

The present invention relates to the field of solid phase polymer synthesis. More specifically, the invention provides methods and reagents for solid phase synthesis of oligomer arrays which may be used, for example, in screening studies for determination of binding affinity.

The synthesis of biological polymers such as peptides and oligonucleotides has been evolving in dramatic fashion from the earliest stages of solution synthesis to solid phase synthesis of a single polymer to the more recent preparations of libraries having large numbers of diverse oligonucleotide sequences on a single solid support or chip.

The evolution of solid phase synthesis of biological polymers began with the early "Merrifield" solid phase peptide synthesis, described in Merrifield, *J. Am. Chem. Soc.* 85:2149–2154 (1963), incorporated herein by reference for all purposes. Solid-phase synthesis techniques have also been provided for the synthesis of several peptide sequences on, for example, a number of "pins." See e.g., Geysen et al., *J. Immun. Meth.* 102:259–274 (1987), incorporated herein by reference for all purposes. Other solid-phase techniques involve, for example, synthesis of various peptide sequences on different cellulose disks supported in a column. See Frank and Doting, *Tetrahedron* 44:6031–6040 (1988), incorporated herein by reference for all purposes. Still other solid-phase techniques are described in U.S. Pat. No. 4,728,502 issued to Hamill and WO 90/00626 (Beattie, inventor).

Each of the above techniques produces only a relatively low density array of polymers. For example, the technique described in Geysen et al. is limited to producing 96 different polymers on pins spaced in the dimensions of a standard microtiter plate.

Improved methods of forming large arrays of oligonucleotides, peptides and other polymer sequences in a short period of time have been devised. Of particular note, Pirrung et al., U.S. Pat. No. 5,143,854 (see also PCT Application No. WO 90/15070) and Fodor et al., PCT Publication No. WO 92/10092, all incorporated herein by reference, disclose methods of forming vast arrays of peptides, oligonucleotides and other polymer sequences using, for example, light-directed synthesis techniques. See also, Fodor et al., *Science*, 251:767–777 (1991), also incorporated herein by reference for all purposes. These procedures are now referred to as VLSIPS™ procedures.

In the above-referenced Fodor et al., PCT application, an elegant method is described for using a computer-controlled system to direct a VLSIPS™ procedure. Using this approach, one heterogenous array of polymers is converted, through simultaneous coupling at a number of reaction sites, into a different heterogenous array. See U.S. Pat. No. 5,384,261 and application Ser. No. 07/980,523, now abandoned, the disclosures of which are incorporated herein for all purposes.

The development of VLSIPS™ technology as described in the above-noted U.S. Pat. No. 5,143,854 and PCT patent publication Nos. WO 90/15070 and 92/10092, is considered pioneering technology in the fields of combinatorial synthesis and screening of combinatorial libraries. More recently, patent application Ser. No. 08/082,937, filed Jun. 25, 1993, describes methods for making arrays of oligonucleotide probes that can be used to provide a partial or complete sequence of a target nucleic acid and to detect the presence of a nucleic acid containing a specific oligonucleotide sequence.

SUMMARY OF THE INVENTION

The present invention provides new compounds, compositions and methods which find application in solid phase synthesis including the preparation of high-density arrays of diverse polymer sequences such as diverse peptides and oligonucleotides as well as in preparation of arrays of small ligand molecules. The compounds of the present invention are those which are typically referred to as linking groups, linkers or spacers.

According to a first aspect of the invention, novel compounds are provided which are useful as linking groups in solid phase polymer synthesis. Additionally, these compounds when used in the solid phase preparation of peptides and oligonucleotides provide improved presentation of the polymers in subsequent assays and diagnostic applications. In one group of embodiments, the compounds are polyether derivatives which vary not only in their hydrophilicities, but also provide varying degrees of solvation-flexibility-"bindability". In another group of embodiments, the compounds are useful as linking groups which are photochemically cleavable.

According to another aspect of the invention, improvements to the coupling chemistry used in the light-directed methods of the VLSIPS™ process are provided. In one embodiment, additional reagents are provided which provide increased yields of the desired products.

According to yet another aspect of the invention, methods are provided for determining the fidelity of polymer synthesis which occurs on a solid support.

A farther understanding of the nature and advantages of the inventions herein may be realized by reference to the remaining portions of the specification and the attached drawings.

BRIEF DESCRIPTION OF THE DRAWINGS

FIGS. 2A and 2B show the reactions which produce the two thiazolidinones. FIGS. 2C and 2D show the HPLC chromatograms of the resulting thiazolidinones and illustrate the purity of each.

DETAILED DESCRIPTION OF THE INVENTION

CONTENTS

Figure 1:
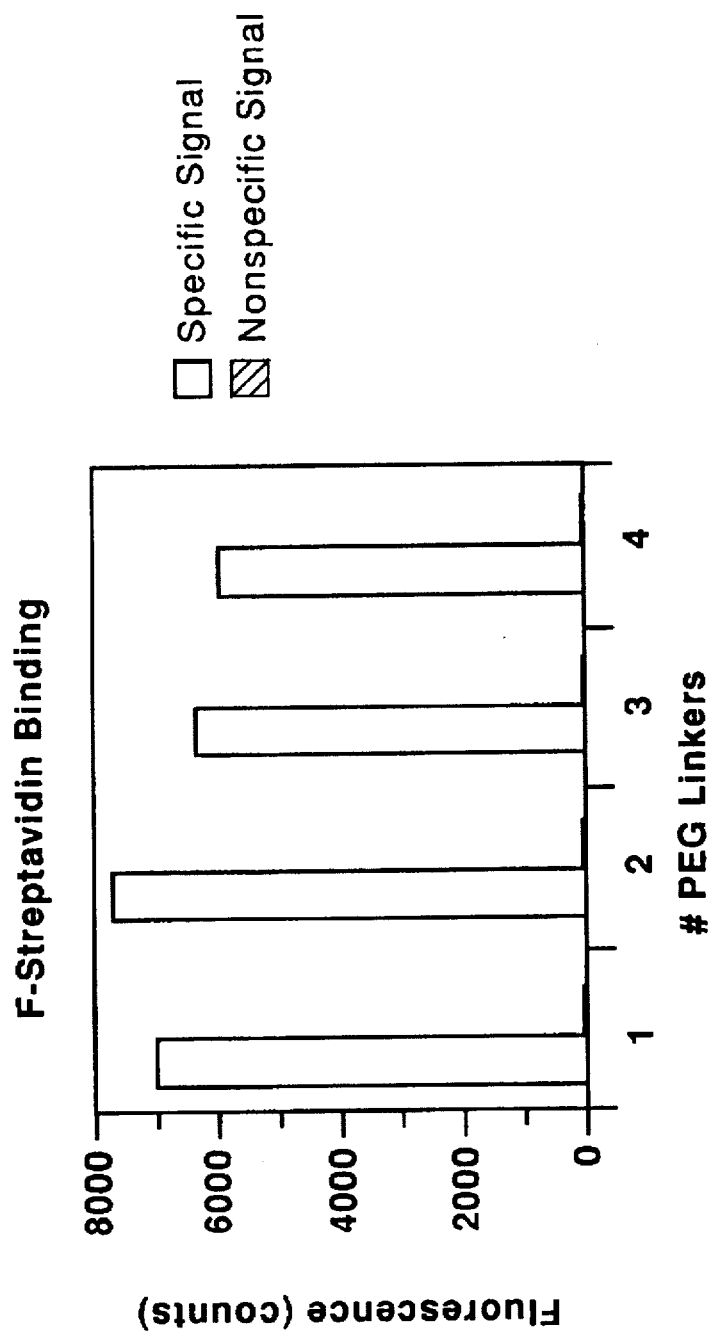
FIG. 1 is a bar graph illustration of streptavidin binding to a biotin moiety which is tethered to a surface via multiple 15-ATOM-PEG linking groups.
Figure 2B:
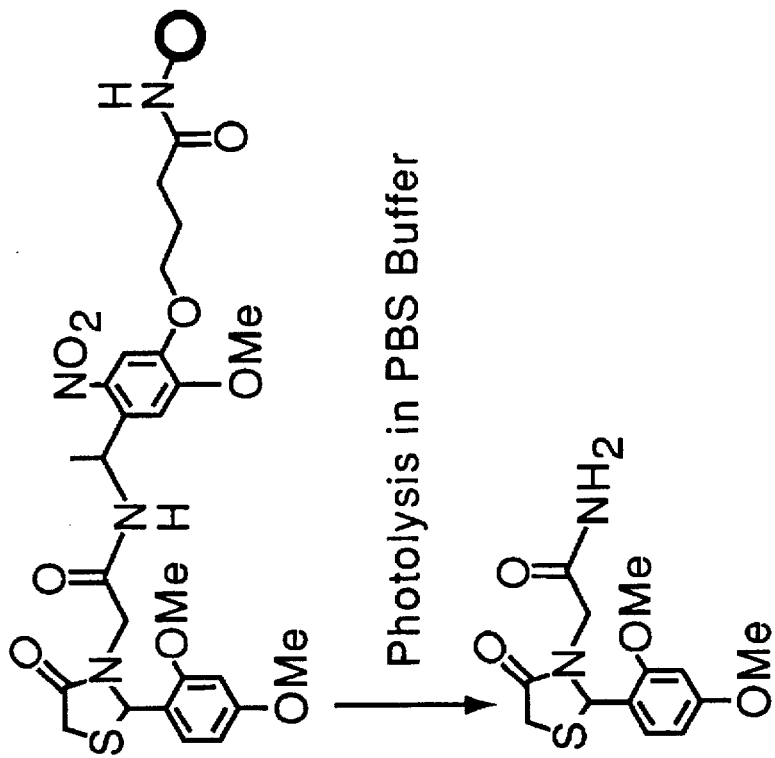
FIGS. 2A–2D illustrate the results achieved by removal of two thiazolidinones from a resin via photolysis. The thiazolidinones were synthesized on a resin having a photocleavable linking group.
Figure 2A:
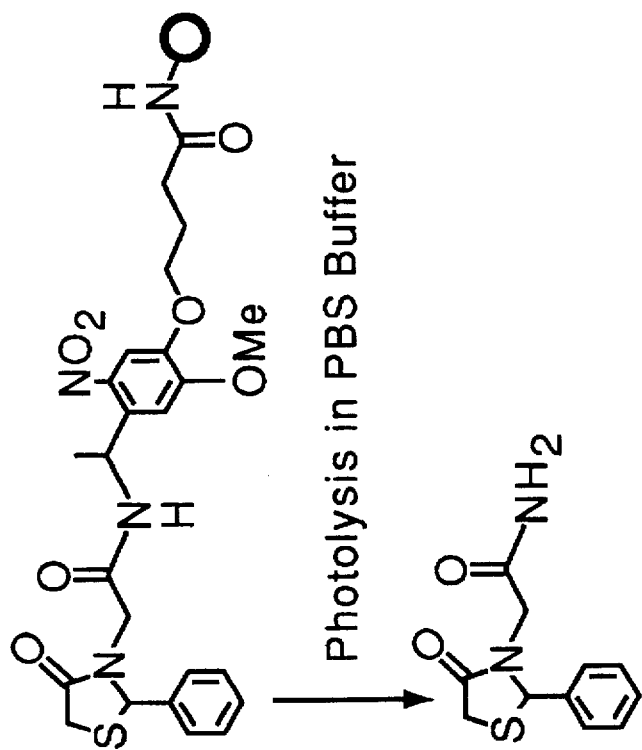
Figure 2D:
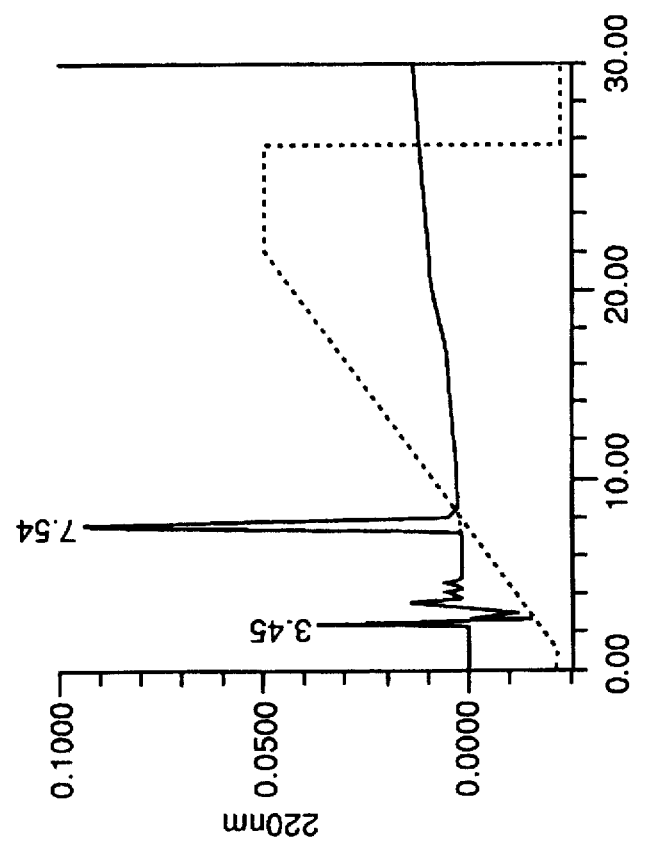
Figure 2C:
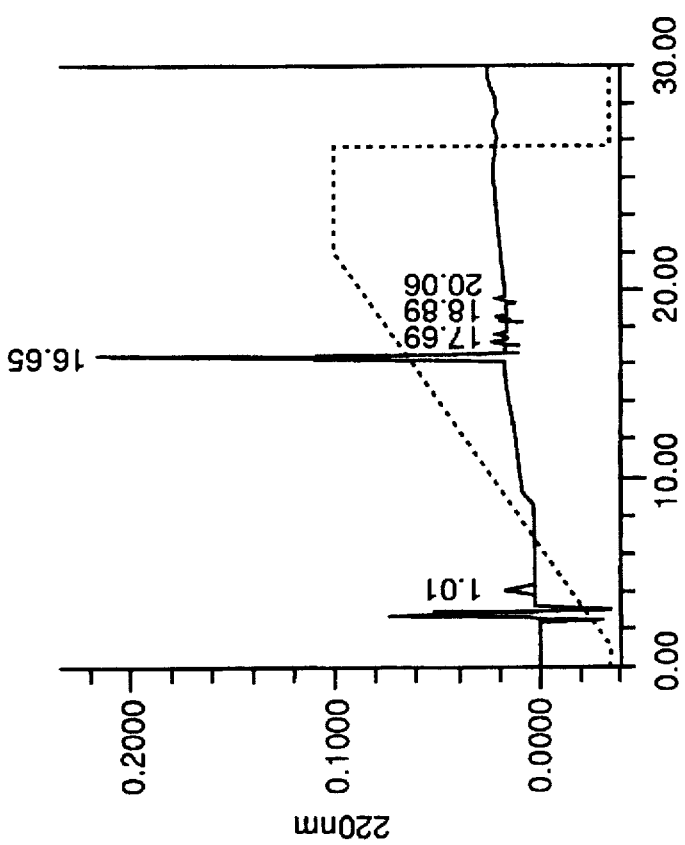

I. Glossary
II. General
III. Novel Linking Groups (Hydrophilic and Photochemical)
IV. Improvements to Solid Phase Coupling Sequences
V. Assays for Determination of Synthesis Fidelity
VI. Examples
VII. Conclusion

I. Glossary

The following abbreviations are used herein: AcOH, acetic acid; ALLOC, allyloxycarbonyl; BOC, t-butoxycarbonyl; BOP, benzotriazol-1-yloxy-tris (dimethylamino)phosphonium hexafluorophosphate; CAP, ε-aminocaproic acid; CHC, 4-aminomethylcyclohexane carboxylic acid; DDZ, 3,5-dimethoxy-αα-dimethylbenzyl; DIEA diisopropylethylamine; DIGLY, glycylglycine; DMF, dimethylformamide; DMT, dimethoxytrityl; DTT, dithiothreitol; EtOAc, ethyl acetate; FMOC, fluorenylmethoxycarbonyl; MeNPOC, α-methylnitro-piperonyloxycarbonyl; MeNVOC, α-methylnitroveratryloxycarbonyl; MP, melting point; NVOC, nitroveratryloxycarbonyl; OBt, hydroxybenzotriazole radical; PBS, phosphate buffered saline; TFA, trifluoroacetic acid; TRIGLY, glycylglycylglycine; UND, ω-aminoundecanoic acid. The abbreviations 15-, 19-, 20- and 24-ATOM-PEG are used to refer to the amino acids (in unprotected form) which are shown in Table I.

The following terms are intended to have the following general meanings as they are used herein:

Chemical Terms

As used herein, the term "alkyl" refers to a saturated hydrocarbon radical which may be straight-chain or branched-chain (for example, ethyl, isopropyl, t-amyl, or 2,5-dimethylhexyl). When "alkyl" or "alkylene" is used to refer to a linking group or a spacer, it is taken to be a group having two available valences for covalent attachment, for example, —CH$_2$CH$_2$—, —CH$_2$CH$_2$CH$_2$—, —CH$_2$CH$_2$CH(CH$_3$)CH$_2$— and —CH$_2$(CH$_2$CH$_2$)$_2$CH$_2$—. Preferred alkyl groups as substituents are those containing 1 to 10 carbon atoms, with those containing 1 to 6 carbon atoms being particularly preferred. Preferred alkyl or alkylene groups as linking groups are those containing 1 to 20 carbon atoms, with those containing 3 to 6 carbon atoms being particularly preferred. The term "polyethylene glycol" is used to refer to those molecules which have repeating units of ethylene glycol, for example, hexaethylene glycol (HO—(CH$_2$CH$_2$O)$_5$—CH$_2$CH$_2$OH). When the term "polyethylene glycol" is used to refer to linking groups and spacer groups, it would be understood by one of skill in the art that other polyethers or polyols could be used as well (i.e., polypropylene glycol or mixtures of ethylene and propylene glycols).

The term "aryl" as used herein, refers to an aromatic substituent which may be a single ring or multiple rings which are fused together, linked covalently or linked to a common group such as an ethylene or methylene moiety. The aromatic rings may each contain heteroatoms, for example, phenyl, naphthyl, biphenyl, diphenylmethyl, 2,2-diphenyl-1-ethyl, thienyl, pyridyl and quinoxalyl. The aryl moieties may also be optionally substituted with halogen atoms, or other groups such as nitro, carboxyl, alkoxy, phenoxy and the like. Additionally, the aryl radicals may be attached to other moieties at any position on the aryl radical which would otherwise be occupied by a hydrogen atom (such as, for example, 2-pyridyl, 3-pyridyl and 4-pyridyl). As used herein, the term "aralkyl" refers to an alkyl group bearing an aryl substituent (for example, benzyl, phenylethyl, 3-(4-nitrophenyl)propyl, and the like).

The term "protecting group" as used herein, refers to any of the groups which are designed to block one reactive site in a molecule while a chemical reaction is carded out at another reactive site. More particularly, the protecting groups used herein can be any of those groups described in Greene, et al., *Protective Groups In Organic Chemistry*, 2nd Ed., John Wiley & Sons, New York, N.Y., 1991, incorporated herein by reference. The proper selection of protecting groups for a particular synthesis will be governed by the overall methods employed in the synthesis. For example, in "light-directed" synthesis, discussed below, the protecting groups will be photolabile protecting groups such as dimethoxybenzoin, NVOC, MeNPOC, and those disclosed in co-pending Application PCT/15S93/10162 (filed Oct. 22, 1993), incorporated herein by reference. In other methods, protecting groups may be removed by chemical methods and include groups such as FMOC, DMT and others known to those of skill in the art.

The term "protected amino acid" refers to an amino acid, typically an α-amino acid having either or both the amine functionality and the carboxylic acid functionality suitably protected by one of the groups described above. Additionally, for those amino acids having reactive sites or functional groups on a side chain (i.e., serine, tyrosine, glutamic acid), the term "protected amino acid" is meant to refer to those compounds which optionally have the side chain functionality protected as well.

The term "activating agent" refers to those groups which, when attached to a particular functional group or reactive site, render that site more reactive toward covalent bond formation with a second functional group or reactive site. For example, the group of activating groups which are useful for a carboxylic acid include simple ester groups and anhydrides. The ester groups include alkyl, aryl and alkenyl esters and in particular such groups as 4-nitrophenyl, N-hydroxylsuccinimide and pentafluorophenol. Other activating agents are known to those of skill in the art.

Ligand

A ligand is a molecule that is recognized by a receptor. Examples of ligands which can be synthesized using the methods and compounds of this invention include, but are not restricted to, agonists and antagonists for cell membrane receptors, toxins and venoms, viral epitopes, hormones, opiates, steroids, peptides, enzyme substrates, cofactors, drugs, lectins, sugars, oligonucleotides, nucleic acids, oligosaccharides, and proteins.

Monomer

A monomer is a member of the set of small molecules which are or can be joined together to form a polymer or a compound composed of two or more members. The set of monomers includes but is not restricted to, for example, the set of common L-amino acids, the set of D-amino acids, the set of synthetic and/or natural amino acids, the set of nucleotides and the set of pentoses and hexoses. The particular ordering of monomers within a polymer is referred to herein as the "sequence" of the polymer. As used herein, monomers refers to any member of a basis set for synthesis of a polymer. For example, dimers of the 20 naturally occurring L-amino acids form a basis set of 400 monomers for synthesis of polypeptides. Different basis sets of monomers may be used at successive steps in the synthesis of a polymer. Furthermore, each of the sets may include protected members which are modified after synthesis. The invention is described herein primarily with regard to the preparation of molecules containing sequences of monomers such as amino acids, but could readily be applied in the preparation of other polymers. Such polymers include, for example, both linear and cyclic polymers of nucleic acids, polysaccharides, phospholipids, and peptides having either α, β, or ω-amino acids, heteropolymers in which a known drug is covalently bound to any of the above, polynucleotides, polyurethanes, polyesters, polycarbonates, polyureas, polyamides, polyethyleneimines, polyarylene sulfides, polysiloxanes, polyimides, polyacetates, or other polymers which will be apparent upon review of this disclosure. Such polymers are "diverse" when polymers having different monomer sequences are formed at different predefined regions of a substrate. Methods of cyclization and polymer reversal of polymers are disclosed in U.S. Pat. No.

5,550,215 which is a CIP of U.S. Pat. No. 5,242,974 entitled "POLYMER REVERSAL ON SOLID SURFACES," incorporated herein by reference for all purposes.

Peptide

A peptide is a polymer in which the monomers are amino acids and are joined together through amide bonds, alternatively referred to as a polypeptide. When the amino acids are α-amino acids, either the L-optical isomer or the D-optical isomer may be used. Additionally, unnatural amino acids, for example, β-alanine, phenylglycine and homoarginine are also meant to be included. Peptides are two or more amino acid monomers long and are often more than 20 amino acid monomers long. Standard abbreviations for amino acids are used (e.g., P for proline). These abbreviations are included in Stryer, *Biochemistry.*, Third Ed., 1988, which is incorporated herein by reference for all purposes.

Receptor

A receptor is a molecule that has an affinity for a ligand. Receptors may be naturally-occurring or manmade molecules. They can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants, viruses, cells, drugs, polynucleotides, nucleic acids, peptides, cofactors, lectins, sugars, polysaccharides, cellular membranes, and organelles. Receptors are sometimes referred to in the art as anti-ligands. As the term receptors is used herein, no difference in meaning is intended. A "Ligand Receptor Pair" is formed when two molecules have combined through molecular recognition to form a complex.

Specific examples of receptors which can be investigated using ligands and libraries prepared using the methods and compounds of this invention include but are not restricted to:

a) Microorganism receptors: Determination of ligands that bind to microorganism receptors such as specific transport proteins or enzymes essential to survival of microorganisms would be a useful tool for discovering new classes of antibiotics. Of particular value would be antibiotics against opportunistic fungi, protozoa, and bacteria resistant to antibiotics in current use.

b) Enzymes: For instance, a receptor can comprise a binding site of an enzyme such as an enzyme responsible for cleaving a neurotransmitter; determination of ligands for this type of receptor to modulate the action of an enzyme that cleaves a neurotransmitter is useful in developing drugs that can be used in the treatment of disorders of neurotransmission.

c) Antibodies: For instance, the invention may be useful in investigating a receptor that comprises a ligand-binding site on an antibody molecule which combines with an epitope of an antigen of interest; determining a sequence that mimics an antigenic epitope may lead to the development of vaccines in which the immunogen is based on one or more of such sequences or lead to the development of related diagnostic agents or compounds useful in therapeutic treatments such as for autoimmune diseases (e.g., by blocking the binding of the "self" antibodies).

d) Nucleic Acids: Sequences of nucleic acids may be synthesized to establish DNA or RNA binding sequences that act as receptors for synthesized sequence.

e) Catalytic Polypeptides: Polymers, preferably antibodies, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant. Catalytic polypeptides and others are described in, for example, PCT Publication No. WO 90/05746, WO 90/05749, and WO 90/05785, which are incorporated herein by reference for all purposes.

f) Hormone receptors: Determination of the ligands which bind with high affinity to a receptor such as the receptors for insulin and growth hormone is useful in the development of, for example, an oral replacement of the daily injections which diabetics must take to relieve the symptoms of diabetes or a replacement for growth hormone. Other examples of hormone receptors include the vasoconstrictive hormone receptors; determination of ligands for these receptors may lead to the development of drugs to control blood pressure.

g) Opiate receptors: Determination of ligands which bind to the opiate receptors in the brain is useful in the development of less-addictive replacements for morphine and related drugs.

Substrate

A material having a rigid or semi-rigid surface. In many embodiments, at least one surface of the substrate will be substantially flat, although in some embodiments it may be desirable to physically separate synthesis regions for different polymers with, for example, wells, raised regions, etched trenches, or the like. In some embodiments, the substrate itself contains wells, trenches, flow through regions, etc. which form all or part of the synthesis regions. According to other embodiments, small beads may be provided on the surface, and compounds synthesized thereon may be released upon completion of the synthesis.

Channel Block

A material having a plurality of grooves or recessed regions on a surface thereof. The grooves or recessed regions may take on a variety of geometric configurations, including but not limited to stripes, circles, serpentine paths, or the like. Channel blocks may be prepared in a variety of manners, including etching silicon blocks, molding or pressing polymers, etc.

Predefined Region

A predefined region is a localized area on a substrate which is, was, or is intended to be used for formation of a selected polymer and is otherwise referred to herein in the alternative as "reaction" region, a "selected" region, or simply a "region." The predefined region may have any convenient shape, e.g., circular, rectangular, elliptical, wedge-shaped, etc. In some embodiments, a predefined region and, therefore, the area upon which each distinct polymer sequence is synthesized is smaller than about 1 cm$^2$, more preferably less than 1 mm$^2$, and still more preferably less than 0.5 mm$^2$. In most preferred embodiments the regions have an area less than about 10,000 μm$^2$ or, more preferably, less than 100μm$^2$. Within these regions, the polymer synthesized therein is preferably synthesized in a substantially pure form. Additionally, multiple copies of the polymer will typically be synthesized within any preselected region. The number of copies can be in the thousands to the millions.

Substantially Pure

A polymer is considered to be "substantially pure" within a predefined region of a substrate when it exhibits characteristics that distinguish it from other predefined regions. Typically, purity will be measured in terms of biological activity or function as a result of uniform sequence. Such characteristics will typically be measured by way of binding with a selected ligand or receptor. Preferably the region is sufficiently pure such that the predominant species in the predefined region is the desired sequence. According to preferred aspects of the invention, the polymer is at least 5% pure, more preferably more than 10% to 20% pure, more preferably more than 80% to 90% pure, and most preferably more than 95% pure, where purity for this purpose refers to the ratio of the number of ligand molecules formed in a predefined region having a desired sequence to the total number of molecules formed in the predefined region.

II. General

The compounds, compositions and methods of the present invention can be used in a number of solid phase synthesis applications, including light-directed methods, flow channel and spotting methods, pin-based methods and bead-based methods.

Light-Directed Methods

"Light-directed" methods (which are one technique in a family of methods known as VLSIPS™ methods) are described in U.S. Pat. No. 5,143,854, previously incorporated by reference. The light directed methods discussed in the '854 patent involve activating predefined regions of a substrate or solid support and then contacting the substrate with a preselected monomer solution. The predefined regions can be activated with a light source, typically shown through a mask (much in the manner of photolithography techniques used in integrated circuit fabrication). Other regions of the substrate remain inactive because they are blocked by the mask from illumination and remain chemically protected. Thus, a light pattern defines which regions of the substrate react with a given monomer. By repeatedly activating different sets of predefined regions and contacting different monomer solutions with the substrate, a diverse array of polymers is produced on the substrate. Of course, other steps such as washing unreacted monomer solution from the substrate can be used as necessary.

Flow Channel or Spotting Methods

Additional methods applicable to library synthesis on a single substrate are described in co-pending application Ser. Nos. 07/980,523, filed Nov. 20, 1992, and 07/796,243, filed Nov. 22, 1991, incorporated herein by reference for all purposes. In the methods disclosed in these applications, reagents are delivered to the substrate by either (1) flowing within a channel defined on predefined regions or (2) "spotting" on predefined regions. However, other approaches, as well as combinations of spotting and flowing, may be employed. In each instance, certain activated regions of the substrate are mechanically separated from other regions when the monomer solutions are delivered to the various reaction sites.

A typical "flow channel" method applied to the compounds and libraries of the present invention can generally be described as follows. Diverse polymer sequences are synthesized at selected regions of a substrate or solid support by forming flow channels on a surface of the substrate through which appropriate reagents flow or in which appropriate reagents are placed. For example, assume a monomer "A" is to be bound to the substrate in a first group of selected regions. If necessary, all or part of the surface of the substrate in all or a part of the selected regions is activated for binding by, for example, flowing appropriate reagents through all or some of the channels, or by washing the entire substrate with appropriate reagents. After placement of a channel block on the surface of the substrate, a reagent having the monomer A flows through or is placed in all or some of the channel(s). The channels provide fluid contact to the first selected regions, thereby binding the monomer A on the substrate directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the substrate; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form a vast array of sequences of desired length at known locations on the substrate.

After the substrate is activated, monomer A can be flowed through some of the channels, monomer B can be flowed through other channels, a monomer C can be flowed through still other channels, etc. In this manner, many or all of the reaction regions are reacted with a monomer before the channel block must be moved or the substrate must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the substrate. For example, according to some embodiments, a protective coating such as a hydrophilic or hydrophobic coating (depending upon the nature of the solvent) is utilized over portions of the substrate to be protected, sometimes in combination with materials that facilitate wetting by the reactant solution in other regions. In this manner, the flowing solutions are further prevented from passing outside of their designated flow paths.

The "spotting" methods of preparing compounds and libraries of the present invention can be implemented in much the same manner as the flow channel methods. For example, a monomer A can be delivered to and coupled with a first group of reaction regions which have been appropriately activated. Thereafter, a monomer B can be delivered to and reacted with a second group of activated reaction regions. Unlike the flow channel embodiments described above, reactants are delivered by directly depositing (rather than flowing) relatively small quantities of them in selected regions. In some steps, of course, the entire substrate surface can be sprayed or otherwise coated with a solution. In preferred embodiments, a dispenser moves from region to region, depositing only as much monomer as necessary at each stop. Typical dispensers include a micropipette to deliver the monomer solution to the substrate and a robotic system to control the position of the micropipette with respect to the substrate, or an ink-jet printer. In other embodiments, the dispenser includes a series of tubes, a manifold, an array of pipettes, or the like so that various reagents can be delivered to the reaction regions simultaneously.

Pin-Based Methods

Another method which is useful for the preparation of compounds and libraries of the present invention involves "pin based synthesis." This method is described in detail in U.S. Pat. No. 5,288,514, previously incorporated herein by reference. The method utilizes a substrate having a plurality of pins or other extensions. The pins are each inserted simultaneously into individual reagent containers in a tray. In a common embodiment, an array of 96 pins/containers is utilized.

Each tray is filled with a particular reagent for coupling in a particular chemical reaction on an individual pin. Accordingly, the trays will often contain different reagents. Since the chemistry disclosed herein has been established such that a relatively similar set of reaction conditions may be utilized to perform each of the reactions, it becomes possible to conduct multiple chemical coupling steps simultaneously. In the first step of the process the invention provides for the use of substrate(s) on which the chemical coupling steps are conducted. The substrate is optionally provided with a spacer having active sites. In the particular case of oligonucleotides, for example, the spacer may be selected from a wide variety of molecules which can be used in organic environments associated with synthesis as well as aqueous environments associated with binding studies. Examples of suitable spacers are polyethyleneglycols, dicarboxylic acids, polyamines and alkylenes, substituted with, for example, methoxy and ethoxy groups. Additionally, the spacers will have an active site on the distal end. The active sites are optionally protected initially by protecting groups. Among a wide variety of protecting groups which are useful are FMOC, BOC, t-butyl esters, t-butyl ethers, and the like. Various exemplary protecting groups are described in, for example, Atherton et al., *Solid Phase Peptide Synthesis*, IRL Press (1989), incorporated herein by reference. In some embodiments, the spacer may provide for a cleavable function by way of, for example, exposure to acid or base.

Bead Based Methods

Yet another method which is useful for synthesis of polymers and small ligand molecules on a solid support "bead based synthesis." A general approach for bead based synthesis is described copending application Ser. Nos. 07/762,522 (filed Sep. 18, 1991); 07/946,239 (filed Sep. 16, 1992); 08/146,886 (filed Nov. 2, 1993 now abandoned); U.S. Pat. No. 5,541,061 and PCT/US93/04145 (filed Apr. 28, 1993), the disclosures of which are incorporated herein by reference.

For the synthesis of molecules such as oligonucleotides on beads, a large plurality of beads are suspended in a suitable carrier (such as water) in a container. The beads are provided with optional spacer molecules having an active site. The active site is protected by an optional protecting group.

In a first step of the synthesis, the beads are divided for coupling into a plurality of containers. For the purposes of this brief description, the number of containers will be limited to three, and the monomers denoted as A, B, C, D, E, and F. The protecting groups are then removed and a first portion of the molecule to be synthesized is added to each of the three containers (i.e., A is added to container 1, B is added to container 2 and C is added to container 3).

Thereafter, the various beads are appropriately washed of excess reagents, and remixed in one container. Again, it will be recognized that by virtue of the large number of beads utilized at the outset, there will similarly be a large number of beads randomly dispersed in the container, each having a particular first portion of the monomer to be synthesized on a surface thereof.

Thereafter, the various beads are again divided for coupling in another group of three containers. The beads in the first container are deprotected and exposed to a second monomer (D), while the beads in the second and third containers are coupled to molecule portions E and F respectively. Accordingly, molecules AD, BD, and CD will be present in the first container, while AE, BE, and CE will be present in the second container, and molecules AF, BF, and CF will be present in the third container. Each bead, however, will have only a single type of molecule on its surface. Thus, all of the possible molecules formed from the first portions A, B, C, and the second portions D, E, and F have been formed.

The beads are then recombined into one container and additional steps such as are conducted to complete the synthesis of the polymer molecules. In a preferred embodiment, the beads are tagged with an identifying tag which is unique to the particular double-stranded oligonucleotide or probe which is present on each bead. A complete description of identifier tags for use in synthetic libraries is provided in co-pending application Ser. No. 08/146,886 (filed Nov. 2, 1993 now abandoned) previously incorporated by reference for all purposes.

The advent of methods for the synthesis of diverse chemical compounds on solid supports has resulted in the genesis of a multitude of diagnostic applications for such chemical libraries. A number of these diagnostic applications involve contacting a sample with a solid support, or chip, having multiple attached biological polymers such as peptides and oligonucleotides, or other small ligand molecules synthesized from building blocks in a stepwise fashion, in order to identify any species which specifically binds to one or more of the attached polymers or small ligand molecules.

For example, patent application Ser. No. 08/082,937, filed Jun. 25, 1993, now abandoned describes methods for making arrays of oligonucleotide probes that can be used to provide the complete sequence of a target nucleic acid and to detect the presence of a nucleic acid containing a specific oligonucleotide sequence. U.S. Pat. No. 5,556,752 describes methods of making arrays of unimolecular, double-stranded oligonucleotides which can be used in diagnostic applications involving protein/DNA binding interactions such as those associated with the p53 protein and the genes contributing to a number of cancer conditions. Arrays of double-stranded oligonucleotides can also be used to screen for new drugs having particular binding affinities.

A number of factors contribute to the successful synthesis and use of oligomer arrays on solid supports. For example, issues of relevance to the use of derivatized glass substrates for carrying out VLSIPS synthesis of peptide arrays are the spacing of the synthesis initiation sites, the wettability of the surface by organic solvents and aqueous solutions, and the extent to which non-specific binding of receptors, antibodies or other biological macromolecules occurs.

The spacing of the synthesis initiation sites (typically, primary amines) is of concern since very high site densities will affect binding events between tethered ligands and receptors. Additionally, increased yields in synthesis can be achieved by control of phenomena such as free radical formation during photolytic reaction, solvent accessibility and surface electrostatic effects.

It will be apparent to those of skill in the art that certain aspects of the present invention will find application in all methods of solid phase polymer synthesis, whereas other aspects of the invention will find application in only particular methods of solid phase synthesis. For example, compounds of the present invention which are useful as hydrophilic linking groups are useful in all of the above solid phase techniques. Other compounds such as the photolabile linking groups will find application more preferably in methods involving "flow channel" and "spotting" techniques, "bead-based" synthesis and "pin-based" synthesis.

Other aspects of the present invention involving conditions and reagents for removing the NVOC protecting group will be directed primarily to the light-directed synthesis described in, for example, U.S. Pat. No. 5,143,854.

Still other methods for determining the fidelity of polymer synthesis will find application in all solid phase techniques.

III. Novel Linking Groups

The use of VLSIPS and ESL technologies, disclosed in U.S. Pat. No. 5,143,854, and U.S. patent application Ser. Nos. 07/946,239 and 08/146,886 now abandoned, and incorporated herein by reference for all purposes, often requires that the support used to assemble the ligands also be used to display the ligands for biological binding experiments. As a result, any linking groups used in preparation of the ligands must perform well in the organic environment used in synthesizing the ligands as well as the aqueous environment typically used in binding assays.

Thus, in one aspect, the present invention provides novel linking groups which can facilitate polymer synthesis on a solid support and which provide other advantageous properties for biological assays. Some of the linking groups are hydrophilic and provide a "wettable" surface which aids in synthesis of the polymers as well as in screening of the polymers for activity. Still other linking groups are more hydrophobic.

One group of "hydrophilic" compounds which can be used as linking groups are represented by the formula:

P—X—Y in which P is a protecting group, X is a polymer chain having amine functional groups at the termini, and Y is a radical of formula:

—CO—Z—CO$_2$R in which Z is an alkyl radical having from 1 to 10 carbon atoms, and R is hydrogen or an activating group.

In one group of embodiments, P is a photocleavable protecting group, preferably an NVOC, MeNPOC, Dimethoxybenzoinyl, or DDZ. More preferably, P is a MeNPOC protecting group.

In another group of embodiments, P is FMOC or BOC.

In still another group of embodiments, X is a polyether chain having an amine functionality at the termini. Preferably, X is —NH—(CH$_2$CH$_2$O)$_n$CH$_2$CH$_2$NH—, —NH—CH$_2$(CH$_2$CH$_2$O)$_n$CH$_2$CH$_2$CH$_2$NH—, —NH—CH$_2$(CH$_2$CH$_2$CH$_2$O)$_n$CH$_2$CH$_2$CH$_2$NH— or —NH—(CH$_2$)$_m$O(CH$_2$)$_n$O(CH$_2$)$_m$NH—, in which n is an integer of from 1 to 10 and m is an integer of from 1 to 6.

In yet another group of embodiments, Z is an alkyl radical of formula —(CH$_2$)$_q$— in which q is an integer of from 1 to 6.

In a particularly preferred embodiment, P is MeNPOC or FMOC, X is —NH—(CH$_2$CH$_2$O)$_2$CH$_2$CH$_2$NH— and Y is —CO—(CH$_2$)$_3$—CO$_2$H.

The hydrophilic linking groups of the present invention can be synthesized by methods which are known to those of skill in the art. For example, commercially available hexaethylene glycol (Aldrich Chemical Company, Milwaukee, Wis. USA) can be treated with p-toluenesulfonyl chloride and ammonia to produce a glycol derivative having amino groups at the chain termini. Treatment of the diamine with glutaric anhydride, followed by protection of the remaining amino group with, for example, NVOC-Cl produces a protected form of the linking group referred to as 24-ATOM-PEG (see Table 1, Example 2). Other methods for the synthesis of hydrophilic linking groups begin with pentaethylene glycol and proceed with a one carbon homologation on each termini via treatment of the diol with p-toluenesulfonyl chloride followed by cyanide ion. Reduction of the resultant dinitrile provides a diamine which can be treated with glutaric anhydride followed by protection of the remaining amine to provide a protected form of the linking group referred to as 20-ATOM-PEG (see Table 1, Example 2). Still other diamines which are useful in the present linking groups are available from Fluka Chemical Co. (Ronkonkoma, N.Y., USA).

In another aspect, the present invention provides novel compounds which are useful as photochemically cleavable linking groups. Linking groups which are photochemically cleavable are useful in several applications. In one application, these linking groups can be used for the photoinduced release of oligomers or small ligand molecules from a surface for characterization purposes following a bioassay. In another application, such linking groups are useful for the mild cleavage of oligomers from a surface after various side chain protecting groups are removed. The oligomers can then be used in subsequent bioassays.

A number of reports of photochemically cleavable linking groups have appeared in the literature for use in peptide synthesis. A phenacyl based linking group (see 1 below) was first disclosed in Wang, *J. Org. Chem.* 41:3258 (1976). An ortho-nitrobenzyl based linking group (see 2 below) was disclosed in Rich, et al., *J. Am. Chem. Soc.* 97:1575–1579 (1975). Both of these have been reported to give modest yields of peptides upon photolytic cleavage from a support, but only after extended photolysis (e.g. 10 hours of photolysis in trifluoroethanol).

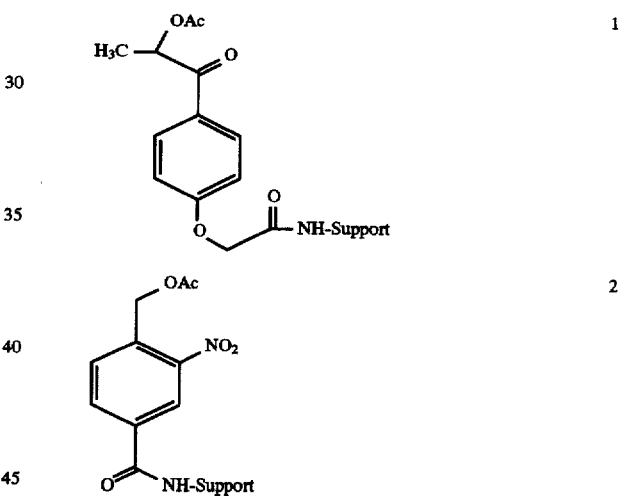

Compounds of the present invention which are useful as photochemically cleavable linking groups are based upon nitroveratryl (NVOC) and α-methylnitroveratryl (MeNVOC) groups and can be represented by the formula:

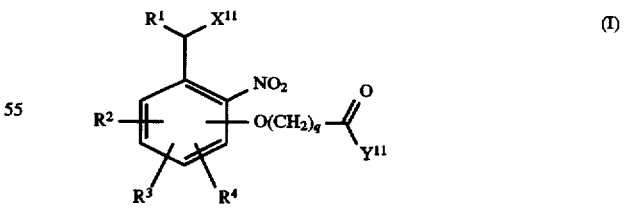

in which R$^1$ is C$_1$–C$_8$ alkyl, aryl or aralkyl; R$^2$, R$^3$ and R$^4$ are each independently hydrogen, C$_1$–C$_8$ alkyl, or C$_1$–C$_8$ alkoxy; X$^{11}$ and Y$_{11}$ are each independently halogen, —SH, —SP, —OH, —OP, —NH$_2$ or —NHP, in which P is a suitable protecting group; and q is an integer of from 1 to 10, preferably from 1 to 4.

In one group of embodiments, the compounds are represented by the formula:

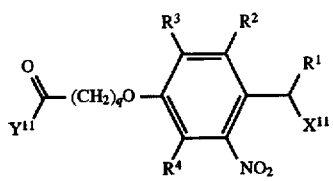

in which $R^1$ is $C_1-C_8$ alkyl; $R^2$ and $R^4$ are each independently hydrogen, $C_1-C_8$ alkyl or $C_1-C_8$ alkoxy; $R^3$ is $C_1-C_8$ alkoxy; $X^{11}$ and $Y^{11}$ are each independently —Br, —Cl, —OH, —NH$_2$, —OP, and —NHP, wherein P is a suitable protecting group; and q is an integer of from 1 to 4. In particularly preferred embodiments, $R^1$ is methyl, $R^2$ and $R^4$ are both hydrogen, $R^3$ is methoxy, $Y^{11}$ is —OH, q is 3, and $X^{11}$ is —Br, —OH, —NH$_2$, —ODMT, —NHBOC or —NHFMOC.

In another group of embodiments, the compounds are represented by the formula:

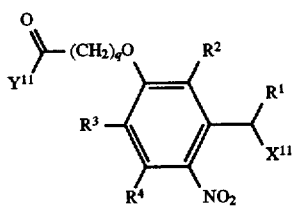

in which the symbols $R^1$, $R^2$, $R^3$, $R^4$, $X^{11}$, $Y^{11}$ and q represent those groups described above for the first group of embodiments. As above, embodiments which are particularly preferred are those in which $R^1$ is methyl, $R^2$ and $R^4$ are both hydrogen, $R^3$ is methoxy, $Y^{11}$ is —OH, q is 3, and $X^{11}$ is —Br, —OH, —NH$_2$, —ODMT, —NHBOC or —NHFMOC.

Exemplary of the photochemically cleavable linking groups of the present invention are structures 3–6, below.

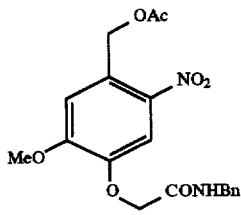

3

4

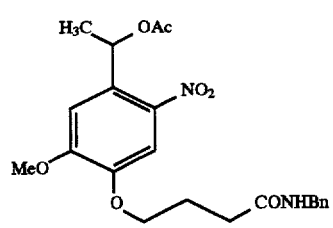

5

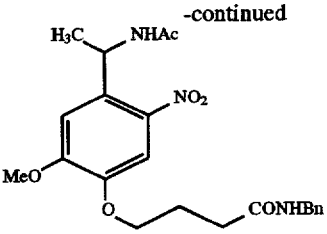

6

Compounds 3–6 were prepared in order to evaluate the effectiveness of each as a linking group. As a result, each compound was provided with an amide linkage (—CONHBn) on one terminus to represent the linking moiety on a support and an ester (—OAc) or amide (—NHAc) linkage on the other terminus. One of skill in the art will appreciate that these photochemically cleavable linking groups can be prepared and stored in their unprotected forms as hydroxy-acids or amino-acids, or they can be provided with protecting groups which are suitable for a variety of synthetic applications. These compounds which are suitable as photochemically cleavable linking groups can be prepared by standard synthetic methods known to those of skill in the art. For example, linking group 3 can be prepared from commercially available vanillin (Aldrich Chemical Company, Milwaukee, Wis., USA). Alkylation the hydroxyl functionality of vanillin with t-butyl bromoacetate provides a phenoxyacetic ester derivative which can be nitrated using nitric acid. The carboxylic acid functionality which is formed via ester cleavage during the nitration process can be convened to the benzamide using standard methods. Reduction of the aldehyde with sodium borohydride followed by acylation of the hydroxyl group thus formed with acetic anhydride provides linking group 3.

Preparation of linking group 4 can be achieved in a similar sequence of steps beginning with acetovallinone (Aldrich Chemical Company). Preparation of linking group 5 can be achieved using methods similar to those employed for linking group 4, by substituting t-butyl 4-bromobutyrate for t-butyl bromoacetate. Preparation of 6 can be achieved by reductive amination of the keto-acid intermediate used in the preparation of 5. Following amination, the resultant amine is protected as its acetamide and the carboxylic acid functionality is converted to a benzamide to provide 6.

Linking groups similar to 3 and 4, but having —NH—FMOC in place of —OAc can also be prepared using known methods. For example, the aldehyde-acid formed in the preparation of 3 can be treated under reductive amination conditions to provide an aminomethyl substituent in place of the aldehyde functionality. Protection of the amine with FMOC-Cl can be carried out according to known procedures to provide linking group 7. Similarly, 8 can be prepared via reductive amination of the keto-acid prepared in the synthesis of 4, followed by amino group protection with FMOC-Cl. Other protecting groups which are also suitable include, for example, ALLOC and BOC.

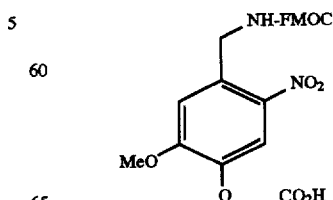

7

-continued

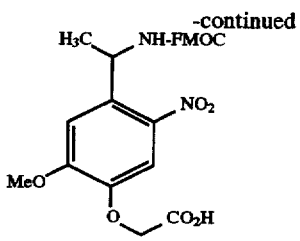
8

In another aspect, the present invention provides compositions which are solid substrates derivatized with the compounds of the present invention. These derivatized substrates having linking groups such as those "hydrophilic" and "photochemically cleavable" linking groups just described, can be represented by the formula:

A—B—L in which A is a solid substrate, B is a bond or a derivatizing group and L is a linking group.

The solid substrates may be biological, nonbiological, organic, inorganic, or a combination of any of these, existing as particles, strands, precipitates, gels, sheets, tubing, spheres, containers, capillaries, pads, slices, films, plates, slides, etc. The solid substrate is preferably flat but may take on alternative surface configurations. For example, the solid substrate may contain raised or depressed regions on which synthesis takes place. In some embodiments, the solid substrate will be chosen to provide appropriate light-absorbing characteristics. For example, the substrate may be a polymerized Langmuir Blodgett film, functionalized glass, Si, Ge, GaAs, GaP, SiO$_2$, SiN$_4$, modified silicon, or any one of a variety of gels or polymers such as (poly) tetrafluoroethylene, (poly)vinylidendifluoride, polystyrene, polycarbonate, or combinations thereof. Other suitable solid substrate materials will be readily apparent to those of skill in the art. Preferably, the surface of the solid substrate will contain reactive groups, which could be carboxyl, amino, hydroxyl, thiol, or the like. More preferably, the surface will be optically transparent and will have surface Si—OH functionalities, such as are found on silica surfaces.

For those embodiments in which B is a derivatizing group, it will be attached to the solid substrate via carbon-carbon bonds using, for example, substrates having (poly)trifluorochloroethylene surfaces, or more preferably, by siloxane bonds (using, for example, glass or silicon oxide as the solid substrate). Siloxane bonds with the surface of the substrate are formed in one embodiment via reactions of derivatization reagents bearing trichlorosilyl or trialkoxysilyl groups.

The particular derivatizing group is selected based upon its hydrophilic/hydrophobic properties to improve presentation of an attached oligomer to certain receptors, proteins or drugs. As noted above, for the derivatization reagents used in surface engineering, prior to attachment to the solid substrate the derivatizing group will have a substrate attaching group at one end, and a reactive site at the other end. The reactive site will be a group which is appropriate for attachment to the linking group, L. For example, groups appropriate for attachment to a silica surface would include trichlorosilyl and trialkoxysilyl functional groups. Groups which are suitable for attachment to a linking group include amine, hydroxyl, thiol, carboxylic acid, ester, amide, isocyanate and isothiocyanate. Preferred derivatizing groups include aminoalkyltrialkoxysilanes, hydroxyalkyltrialkoxysilanes, polyethyleneglycols, polyethyleneimine, polyacrylamide, polyvinylalcohol and combinations thereof.

The linking groups used in the present compositions which are typically thought of as hydrophilic linking groups are represented by radicals of the formula:

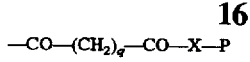

in which P is a protecting group, X is a polymer chain having amine functional groups at the termini, and q is an integer of from 1 to 10, preferably from 1 to 4. In one group of preferred embodiments, P is a photocleavable protecting group, more preferably an NVOC or MeNPOC. For other applications, preferred protecting groups include FMOC or BOC. In another group of preferred embodiments, X is a polyether chain having an amine functionality at the termini. More preferably, X is —NH—(CH$_2$CH$_2$O)$_n$CH$_2$CH$_2$NH—, —NH—CH$_2$(CH$_2$CH$_2$O)$_n$CH$_2$CH$_2$CH$_2$NH—, —NH—CH$_2$(CH$_2$CH$_2$CH$_2$O)$_n$CH$_2$CH$_2$CH$_2$NH— or —NH—(CH$_2$)$_m$O(CH$_2$)$_n$O(CH$_2$)$_m$NH—, in which n is an integer of from 1 to 10 and m is an integer of from 1 to 6. In a particularly preferred embodiment, P is either FMOC or MeNPOC, X is —NH—(CH$_2$CH$_2$O)$_2$CH$_2$CH$_2$NH— and q is 3.

Linking groups used in the present compositions which are photochemically cleavable are represented by radicals of the formula:

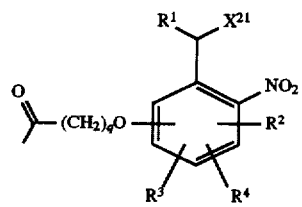

in which $R^1$ is $C_1$-$C_8$ alkyl, aryl or aralkyl; $R^2$, $R^3$ and $R^4$ are each independently hydrogen, $C_1$-$C_8$ alkyl, or $C_1$-$C_8$ alkoxy; $X^{21}$ is halogen, —SH, —SP, —OH, —NH$_2$, —OP or —NHP, wherein P is a suitable protecting group; and q is an integer of from 1 to 10.

In one group of preferred embodiments, L has the formula:

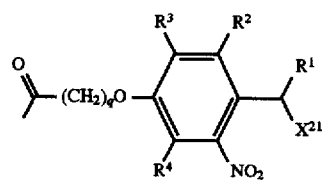

in which $R^1$ is $C_1$-$C_8$ alkyl; $R^2$ and $R^4$ are each independently hydrogen, $C_1$-$C_8$ alkyl or $C_1$-$C_8$ alkoxy; $R^3$ is $C_1$-$C_8$ alkoxy; $X^{21}$ is —Br, —Cl, —OH, —OP, —SH, —SP, —NH$_2$ or —NHP, wherein P is a suitable protecting group; and q is an integer of from 1 to 4. In further preferred embodiments $R^1$ is methyl and $R^3$ is methoxy. More preferably, $R^1$ is methyl, $R^3$ is methoxy, and $R^2$ and $R^4$ are each hydrogen. Still further preferred are those compounds in which n is 3, $R^1$ is methyl, $R^3$ is methoxy, $R^2$ and $R^4$ are each hydrogen, and $X^{21}$ is —NH-FMOC or —NH-BOC.

In another group of preferred embodiments, L has the formula:

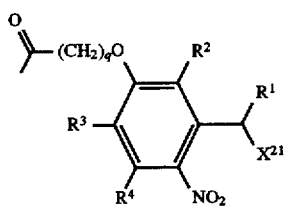

in which the symbols $R^1$, $R^2$, $R^3$, $R^4$, $X^{21}$ and q represent those groups described above for the first group of embodiments. As above, embodiments which are particularly preferred are those in which $R^1$ is methyl and $R^3$ is methoxy. More preferably, $R^1$ is methyl, $R^3$ is methoxy, and $R^2$ and $R^4$ are each hydrogen. Still further preferred are those compounds in which n is 3, $R^1$ is methyl, $R^3$ is methoxy, $R^2$ and $R^4$ are each hydrogen, and $X^{21}$ is —NH-FMOC or —NH-BOC.

The compositions of the present invention can be prepared by standard manipulations of methods already described herein which are well known to those of skill in the art.

In yet another aspect, the present invention provides methods for the preparation of small ligand molecules on a solid support such that the small ligand molecules are removable from the support upon the application of a suitable energy source.

In the first step of the present method, a photolabile linking group is attached to a solid support. The photolabile linking group is represented by the formula:

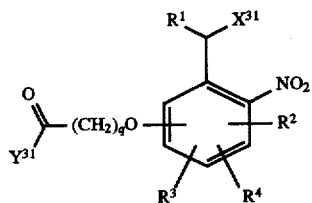

in which $R^1$ is $C_1$–$C_8$ alkyl, aryl or aralkyl; $R^2$, $R^3$ and $R^4$ are each independently hydrogen, $C_1$–$C_8$ alkyl or $C_1$–$C_8$ alkoxy; $X^{31}$ is halogen, —OH, —OP, —SH, —SP, or —NHP and $Y^{31}$ is Br, Cl, OH, $NH_2$, SH, OP, SP and NHP, wherein P is a protecting group; and q is an integer of from 1 to 10. In this step, attachment to the solid support occurs through $Y^{31}$, or alternatively through the carbonyl group attached to $Y^{31}$.

In the second step, protecting groups, where present on $X^{31}$, are removed from the resulting derivatized solid support. In those applications in which a number of diverse small ligand molecules are to be synthesized on the support, the protecting groups may be selectively removed from one region at a time. Methods for this selective removal are described in co-pending application Ser. No. 07/980,523, filed Nov. 20, 1992, now abandoned and U.S. Pat. No. 5,384,261, previously incorporated herein by reference. The removal of protecting groups provides a synthesis initiation site upon which the small ligand molecules can be prepared.

In the third step of the present method, small ligand molecules or polymers are coupled to the synthesis initiation site. The coupling can involve either the attachment of the entire small ligand molecule or polymer, or it can involve the synthesis of the molecules in a stepwise fashion on the synthesis initiation site. In those embodiments in which the molecules are synthesized in stepwise fashion on the synthesis initiation site, the synthesis can proceed by any of the compatible means discussed under the General Methods section.

IV. Alternative Solid Phase Coupling Sequences

In other aspects, the present invention provides alternatives to current methods employed for the light-directed synthesis of polymers such as peptides, oligonucleotides and unimolecular double-stranded oligonucleotides.

"Light directed" methods (also known as VLSIPS™ methods) are described in U.S. Pat. No. 5,143,854, previously incorporated by reference. As noted above in the General section, the light directed methods discussed in the '854 patent involve activating predefined regions of a substrate or solid support and then contacting the substrate with a preselected monomer solution. The predefined regions can be activated with a light source, typically shown through a mask (much in the manner of photolithography techniques used in integrated circuit fabrication). Other regions of the substrate remain inactive because they are blocked by the mask from illumination. Thus, a light pattern defines which regions of the substrate react with a given monomer. By repeatedly activating different sets of predefined regions and contacting different monomer solutions with the substrate, a diverse array of polymers is produced on the substrate. Of course, other steps such as washing unreacted monomer solution from the substrate can be used as necessary. The VLSIPS™ methods are generally preferred for making libraries of polymers for screening. While described in a number of patent publications, a brief description of how this technology can be used to make arrays of oligonucleotides is provided for completeness. The surface of a solid support modified with linking groups having photolabile protecting groups (e.g., NVOC or MeNPOC) is illuminated through a photolithographic mask, yielding reactive groups (typically hydroxyl groups) in the illuminated regions. A 3'-O-phosphoramidite activated deoxynucleoside (protected at the 5'-hydroxyl with a photolabile group) is then presented to the surface and coupling occurs at sites that were exposed to light in the previous step. Following capping, and oxidation, the substrate is rinsed and the surface illuminated through a second mask, to expose additional hydroxyl groups for coupling. A second 5'-protected, 3'-O-phosphoramidite activated deoxynucleoside is presented to the surface. The selective photodeprotection and coupling cycles are repeated until the desired set of oligonucleotides is produced.

Photodeprotection of the growing oligomer is typically conducted in an organic solvent containing an acid such as sulfuric acid. When the protecting group is an NVOC group, photodeprotection leads to the production of 6-nitrosoveratraldehyde as an unstable intermediate which, upon acid catalysis, forms 5,6-dimethoxy-2, 1-benzisoxazol-3(1H)-one. Further photolysis of the latter species produces 6,6-azo-bisveratric acid. Azo species are typically formed from nitrene intermediates which have the potential to produce a number of undesirable side reactions. As a result, the present invention provides a number of methods for reducing the amount of the nitrene which is formed.

In one embodiment, the present invention provides a method for the fight-directed synthesis of polymers wherein hydrazine is used in place of sulfuric acid. In preferred embodiments, photodeprotection is conducted in a hydrazine/dioxane (1/100) mixture. The use of a hydrazine/dioxane mixture provides increased yields of the photo-deprotected product than either neat dioxane or a 5.0 m $H_2SO_4$ dioxane solution.

In another embodiment, the present invention provides a method for the light-directed synthesis of polymers wherein nitrene scavengers are added to the reaction mixture. The removal of NVOC groups (and other similar protecting groups) is thought to proceed through a nitrene intermediate.

As a result, addition of nitrene scavengers to the reaction medium provides one method for reducing any potential interference from the nitrenes in the desired synthesis. Nitrenes react with alkenes as described in McConaghy, et al., *J. Am. Chem. Soc.* 89:2357 and 4450 (1967), incorporated herein by reference. Preferred nitrene scavengers include alkenes such as cyclohexene.

In still other embodiments, the present invention provides a method for the light-directed synthesis of polymers wherein light having a more focused wavelength is used. The intermediate species 5,6-dimethoxy-2, 1-benzisoxazol-3(1H)-one which is formed upon photolysis of NVOC protected oligomers has a longest wavelength adsorption at 314 nm. By filtering off the lower wavelengths used in photodeprotection, the further photochemistry of the intermediate species may be avoided while still effecting removal of the protecting group. Preferred wavelengths for photodeprotection of NVOC protected oligomers are from about 345 nm to about 400 nm, more preferably from about 360 nm to about 380 nm, and most preferably about 365 nm.

In other embodiments, an alternative to the above noted use of sulfuric acid is provided. In particular, sulfuric acid can be replaced with methane sulfonic acid which provides deprotection results equivalent to those achieved with sulfuric add, but is less harsh on polymers such as peptides. Additionally, methane sulfonic acid is volatile and may be easily removed from the surface by washing. Furthermore, the milder nature of methane sulfonic acid allows its use in a deprotection mixture with a wide variety of protecting groups. Preferably, methane sulfonic acid is used in mixtures for the removal of such protecting groups as NVOC, MeNPOC, MeNVOC and other ortho-nitrobenzyl protecting groups and linking groups.

V. Assays for Determination of Synthesis Fidelity

In still another aspect, the present invention provides methods for the synthesis of polymers and the determination of synthesis fidelity which occurs on a solid substrate. The methods can be used for a variety of polymers which are synthesized on a solid substrate and result in a product having the formula:

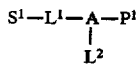

in which $S^1$ is a solid support; $L^1$ is a cleavable bond, spacer or linking group having an optional spacer; A is an attaching group; $L^2$ is a label; and $P^1$ is a polymer which is a peptide, oligonucleotide or other small ligand molecule.

This method comprises first synthesizing a labeled polymer on a solid support. Subsequent cleavage of the labeled polymer from the support and comparison with known standards provides a confirmation of synthesis fidelity. The precise method of synthesis is not critical and can be carried out by any of the solid phase methods described in the General section above. In order to obtain a solid substrate-bound polymer having the formula above, the synthesis will typically proceed by first attaching a linking group or spacer, $L^1$, to the solid support.

As with the compositions of the present invention, the solid supports, or solid substrates can be biological, nonbiological, organic, inorganic, or a combination of any of these, existing as particles, strands, precipitates, gels, sheets, tubing, spheres, containers, capillaries, pads, slices, films, plates, slides, etc. In preferred embodiments, the solid support will have appropriate light-absorbing characteristics such as are provided by a polymerized Langmuir Blodgett film, functionalized glass, Si, Ge, GaAs, GaP, $SiO_2$, $SiN_4$, modified silicon, or any one of a variety of gels or polymers such as (poly)tetrafluoroethylene, (poly)vinylidendifluoride, polystyrene, polycarbonate, or combinations thereof. Preferably, the surface of the solid substrate will contain reactive groups, which could be carboxyl, amino, hydroxyl, thiol, or the like. More preferably, the surface will be optically transparent and will have surface Si—OH functionalities, such as are found on silica surfaces.

The linking groups, or spacers, $L^1$ are not critical but are present to permit subsequent synthesis to proceed without interference from the support. However, the bond, spacer or linking group must be cleavable under conditions which do not degrade the synthesized polymer. The linking groups or spacers, when present (i.e., not a bond) are typically 3–50 atoms long and have a surface attaching portion and a functional group for covalent attachment to the label attaching group. The surface attaching portion is that part of $L^1$ which is directly attached to the solid support. This portion can be attached to the solid support via carbon-carbon bonds using, for example, supports having (poly)trifluorochloroethylene surfaces, or preferably, by siloxane bonds (using, for example, glass or silicon oxide as the solid support). Siloxane bonds with the surface of the support are formed in one embodiment via reactions of surface attaching portions bearing trichlorosilyl or trialkoxysilyl groups. The spacer will also have a site for attachment of the label attaching group. For example, groups which are suitable for attachment to such a group would include amines, hydroxyl, thiol, and carboxyl. Thus, preferred linking groups or spacers, are those molecules derived from aminoalkylsilanes and hydroxyalkylsilanes. In particularly preferred embodiments, the spacer $L^1$ is derived from bis(2-hydroxyethyl)aminopropyl-triethoxysilane, 2-hydroxyethylaminopropyltriethoxysilane, aminopropyltriethoxysilane or hydroxypropyltriethoxysilane.

Attached to the distal end (away from the solid support) is the label attaching group, A. As with $L^1$, the label attaching group can be a variety of structures. However, A will have at least three sites for covalent linkages. One site will be attached to $L^1$, one site will serve at a point of attachment for the label and the third site will serve as a synthesis initiation site for the polymer, $P^1$. Preferably, the site which is attached to $L^1$ will be cleavable following polymer synthesis. Exemplary of such label attaching groups are amino acids having a functional group on the side chain which include lysine, glutamic acid, aspartic acid, arginine, serine, threonine, tyrosine, and cysteine. Non-gene encoded amino acids such as hydroxyproline are also useful. Still other molecules which are useful as attaching groups include synthetic amino acid analogs such as homoserine, homoarginine and the like. As is apparent to one of skill in the art, the stereochemistry of the amino acid is not critical, however a single isomer (either D- or L-) is preferred.

Attached to one of the sites available on the label attaching group is the label, $L^2$. The term "label" refers to a marker which is detectable by spectroscopic means. In preferred embodiments, the label is chromogenic. Suitable chromogens will include molecules and compounds which adsorb light in a distinctive range of wavelengths so that a color may be observed, or emit light when irradiated with radiation of a particular wavelength or wavelength range, e.g., a fluorescent tag.

A wide variety of suitable dyes are available, being primarily chosen to provide an intense color with minimal absorption by their surroundings. Illustrative dye types include quinoline dyes, triarylmethane dyes, acridine dyes, alizarine dyes, phthaleins, insect dyes, azo dyes, anthraquinoid dyes, cyanine dyes, phenazathionium dyes, and phenazoxonium dyes.

A wide variety of fluorescent tags may be employed either by themselves or in conjunction with quencher molecules. Suitable fluorescent tags should be characterized by one or more of the following: high sensitivity, high stability, low background, low environmental sensitivity and high specificity in tagging. Fluorescent tags of interest fall into a variety of categories having certain primary functionalities. These primary functionalities include 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthen, 7-hydroxycoumarin, phenoxazine, calicylate, strophanthidin, porphyrins, triarylmethanes and flavin. Individual fluorescent compounds which have functionalities for linking or which can be modified to incorporate such functionalities include, e.g., dansyl chloride; fluoresceins such as 3,6-dihydroxy-9-phenylxanthhydrol; rhodamineisothiocyanate; N-phenyl 1-amino-8-sulfonatonaphthalene; N-phenyl 2-amino-6-sulfonatonaphthalene; 4-acetamido-4-isothiocyanato-stilbene-2,2'-disulfonic acid; pyrene-3-sulfonic acid; 2-toluidinonaphthalene-6-sulfonate; N-phenyl-N-methyl-2-aminoaphthalene-6-sulfonate; ethidium bromide; stebrine; auromine-0,2-(9'-anthroyl) palmitate; dansyl phosphatidylethanolamine; N,N'-dioctadecyl oxacarbocyanine: N,N'-dihexyl oxacarbocyanine; merocyanine, 4-(3'pyrenyl)stearate; d-3-aminodesoxyequilenin; 12-(9'-anthroyl)stearate; 2-methylanthracene; 9-vinylanthracene; 2,2'(vinylene-p-phenylene) bisbenzoxazole; p-bis(2-(4-methyl-5-phenyl-oxazolyl)) benzene; 6-dimethylamino-1,2-benzophenazin; retinol; bis (3'-aminopyridinium) 1,10-decandiyl diiodide; sulfonaphthylhydrazone of hellibrienin; chlorotetracycline; N-(7-dimethylamino-4-methyl-2-oxo-3-chromenyl) maleimide; N-(p-(2-benzimidazolyl)-phenyl)maleimide; N-(4-fluoranthyl)maleimide; bis(homovanillic acid); resazarin; 4-chloro-7-nitro-2,1,3-benzooxadiazole; merocyanine 540; resorufin; rose bengal; and 2,4-diphenyl-3(2H)-furanone.

Desirably, fluorescent tags should absorb light above about 300 nm, preferably about 350 nm, and more preferably above about 400 nm, usually emitting at wavelengths greater than about 10 nm higher than the wavelength of the light absorbed. It should be noted that the absorption and emission characteristics of the bound dye may differ from the unbound dye. Therefore, when referring to the various wavelength ranges and characteristics of the dyes, it is intended to indicate the dyes as employed and not the dye which is unconjugated and characterized in an arbitrary solvent.

Fluorescent tags are generally preferred because by irradiating a fluorescent tag with light, one can obtain a plurality of emissions. Thus, a single label can provide for a plurality of measurable events.

Detectable signal may also be provided by chemiluminescent and bioluminescent sources. Chemiluminescent sources include a compound which becomes electronically excited by a chemical reaction and may then emit light which serves as the detectible signal or donates energy to a fluorescent acceptor. A diverse number of families of compounds have been found to provide chemiluminescence under a variety or conditions. One family of compounds is 2,3-dihydro-1,4-phthalazinedione. The most popular compound is luminol, which is the 5-amino compound. Other members of the family include the 5-amino-6,7,8-trimethoxy- and the dimethylamino[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents. Chemiluminescence may also be obtained with oxalates, usually oxalyl active esters, e.g., p-nitrophenyl and a peroxide, e.g., hydrogen peroxide, under basic conditions. Alternatively, luciferins may be used in conjunction with luciferase or lucigenins to provide bioluminescence.

In particularly preferred embodiments of the invention, the attaching group is L-lysine and the label is a Dabsyl or Dansyl group.

Finally, a polymer, $P^1$ is attached to or synthesized on the third site of the attaching group. The polymer can be a peptide, oligonucleotide, carbohydrate, or some small ligand molecule such as a β-turn mimetic, prostaglandin or benzodiazepine which can also be synthesized in a stepwise fashion on a solid support.

Following synthesis of the attached labeled polymer or small ligand molecule, the fidelity of synthesis can be determined by cleaving the labeled polymer or small ligand molecule from the solid support, subjecting the labeled species to high performance liquid chromatography, and comparing the resultant chromatogram with a chromatogram from a standard which is synthesized by alternative methods.

In alternative embodiments, a suitable tag can be incorporated during other stages of polymer synthesis. Thus, tags or labels may be incorporated as a last step in synthesis to provide, for example, a peptide having a label or tag attached to the amino terminus. Similarly, a label or tag can be attached to a specific functionality which is present in the support-bound polymer (i.e., attached to the side chain amine of a lysine, the side chain thiol of a cysteine, or other suitable side chain functionality in a peptide of interest).

VI. EXAMPLES

Example 1

This example illustrates the synthesis of FMOC-15-ATOM-PEG (a) Preparation of N-Glutaryl-2,2'-(ethylenedioxy) diethylamine, 9.

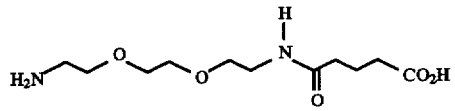

To a solution of 2,2'-(ethylenedioxy)-diethylamine (75 mL, 511 mmol) (Fluka Chemie AG, Switzerland) in 1L of dry p-dioxane was slowly added a solution of glutaric anhydride (11.4 g, 100 mmol) in 100 mL of dry p-dioxane over 1 hour. A viscous white oil formed during the reaction. The solvent was decanted and the oil was triturated with acetone, followed by trituration twice with ethyl ether (until ether phase remains clear). This oily residue was then carried on to the next step without further purification.

(b) Preparation of N'-FMOC-N-glutaryl-2,2'-(ethylenedioxy)diethylamine, 10

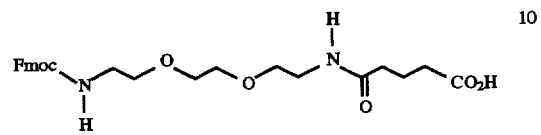

A slurry containing the amino acid 9 from above, diisopropylethylamine (52 mL, 299 mmol) and trimethylsilyl chloride (25 mL, 197 mmol) in 300 mL of $CH_2Cl_2$ was heated to reflux for 3 h, during which time the solution became homogeneous. The reaction mixture was cooled to 0° C. and FMOC-Cl (27 g, 104 mmol) was added over a four hour period in three equal aliquots. The reaction mixture was allowed to warm to room temperature and stirred for an additional 3 h. The solvent was removed under reduced pressure and the residue was partitioned between Et₂O and 5% NaHCO₃. The organic phase was discarded and the aqueous phase was acidified to pH 2 with 1N HCl, and extracted with EtOAc. The organic extract was washed (1N HCl and saturated NaCl), dried (MgSO₄), and evaporated to dryness under reduced pressure. Chromatography on silica gel (5% to 20% AcOH in EtOAc) afforded 32.7 g (65% yield for two steps) of the desired product 10 as a colorless oil which slowly solidified.

Example 2

This example illustrates the evaluation of a number of linking groups for their relative hydrophilicities.

Ten NVOC-protected linking groups having the structures provided in Table 1 below were investigated.

TABLE 1

NVOC-Protected Linking Groups

| Abbreviation | Structure |
|---|---|
| CAP | NVOC—NH–(CH₂)₄–C(O)OH |
| CHC | NVOC—NH–CH₂–(cyclohexyl)–C(O)OH |
| UND | NVOC—NH–(CH₂)₉–C(O)OH |
| GLY | NVOC—NH–CH₂–C(O)OH |
| DIGLY | NVOC—NH–CH₂–C(O)–NH–CH₂–C(O)OH |
| TRIGLY | NVOC—NH–CH₂–C(O)–NH–CH₂–C(O)–NH–CH₂–C(O)OH |
| 15-ATOM-PEG | NVOC—NH–CH₂CH₂–O–CH₂CH₂–O–CH₂CH₂–NH–C(O)–CH₂CH₂–C(O)OH |
| 19-ATOM-PEG | NVOC—NH–(CH₂)₃–O–(CH₂)₃–O–(CH₂)₃–NH–C(O)–CH₂CH₂–C(O)OH |
| 20-ATOM-PEG | NVOC—NH–(CH₂)₃–O–CH₂CH₂–O–(CH₂)₃–NH–C(O)–CH₂CH₂–C(O)OH |
| 24-ATOM-PEG | NVOC—NH–CH₂CH₂–O–CH₂CH₂–O–CH₂CH₂–O–CH₂CH₂–O–CH₂CH₂–NH–C(O)–CH₂CH₂–C(O)OH |

The ten NVOC-protected linking groups were individually dissolved in 50% acetonitrile/water at approximately 1 mM concentrations and 10 μmL of each solution was injected onto a 4.6 mm×25 cm Alltech C₁₈ reverse phase column at 1 mL/minute flow rate under two solvent compositions: 30% CH3CN (0.1% TFA)/H20 (0.1% TFA) or 50% CH₃CN (0.1% TFA)/H₂O (0.1% TFA). The detector was set at 220 nm wavelength. The retention times are tabulated in Table 2, below. The order of elution serves as a measure of relative hydrophilicity of the linkers. The amide-based triglycine (TRIGLY) and diglycine (DIGLY) eluted first and are hence the most hydrophilic. The 15-ATOM-PEG and 24-ATOM-PEG linkers were observed to be slightly less hydrophilic than the amide linkers, but were much more hydrophilic than the hydrocarbon-based linkers CAP, CHC and UND.

TABLE 2

Retention Times and Relative Hydrophilicities of NVOC-Protected Linking Groups

| Compound | Retention time* (50% CH$_3$CN) | Retention time* (30% CH$_3$CN) | Rank** |
|---|---|---|---|
| CAP | 4.63 | 12.31 | 8 |
| CHC | 4.92 | 15.10 | 9 |
| UND | 9.94 | >30 | 10 |
| GLY | 3.92 | 7.37 | 5 |
| DIGLY | 3.44 | 5.42 | 2 |
| TRIGLY | 3.16 | 4.60 | 1 |
| 15-ATOM-PEG | 3.61 | 6.52 | 3 |
| 19-ATOM-PEG | 4.21 | 10.58 | 7 |
| 20-ATOM-PEG | 3.78 | 8.06 | 6 |
| 24-ATOM-PEG | 3.62 | 7.15 | 4 |

*in minutes
**based on retention time in 30% acetonitrile

Example 3

This example illustrates the influence of linker length on the binding of a receptor to a support-bound substrate.

An experiment was conducted to examine the effect of linker length on the binding of streptavidin to biotinylated surfaces. Four surfaces were prepared which differed only in the number of 15-ATOM-PEG linkers coupled onto each other. Following deprotection of the terminal FMOC group, biotin was covalently coupled to the surfaces and both specific and non-specific binding of labeled streptavidin (mixture of FITC-labeled and unlabeled) to the resulting surfaces was determined. FIG. 1 shows the observed values. In general little effect of multiple linkers was observed, although the total amount of specific binding did decrease slightly with increasing number of 15-ATOM-PEG linkers.

Example 4

This example illustrates the ability of various linkers to influence the proteolytic behavior of an enzyme acting on peptides bound to a surface by the various linkers.

Six slides were prepared having three different linking groups: two with 15-ATOM-PEG, two with TRIGLY and two with CAP. One of each of the three types of resulting slides were then deprotected and an additional amino acid coupled onto it to create the corresponding dimers. The six surfaces were thus CAP, CAP-CAP, 15-ATOM-PEG, 15-ATOM-PEG-15-ATOM-PEG, TRIGLY and TRIGLY—TRIGLY. The NVOC-groups were removed from the surface-bound linkers and a template was clamped onto the surface of each slide which segregated the surface into 32 individual wells. A Buna-N gasket was used to seal the template to the surface. Three different pentapeptides protected on their N-terminus as acetates (Ac-GGLAG-OH, Ac-GALAG-OH, Ac-GFLAG-OH) were then coupled to separate wells via BOP/HOBt activation at 5 mM concentration for 12 hours. After extensive washing to remove excess peptides, the wells were capped with acetic anhydride in DMF for 2 hours.

The ability of the linkers to influence the proteolytic behavior of an enzyme was then evaluated with commercially available thermolysin. Thermolysin has been extensively used as a prototypic protease enzyme and the substrate specificity has been well established; it was therefore expected that cleavage would occur between the phenylalanine (F) and leucine (L) residues in the GFLAG substrate. Incorporation of either a glycine (G) or alanine (A) residue in the GGLAG and GALAG peptides, respectively, was anticipated to lead to poorer substrates. Control experiments measuring proteolysis rates ($k_{cat}/K_m$ values) for the three peptides in solution confirmed these results, and the relative proteolysis rates in solution were determined to be GFLAG>GALAG>GGLAG.

The surface assay involved incubating the surface-bound peptides with thermolysin for specific times and concentrations, followed by extensive washing of the surface with buffer. The liberated amino groups (resulting from cleavage of the peptide to generate most likely H$_2$N-LAG-Linker-Surface) were then labeled with a fluorescent tag (FITC) and the surface-bound fluorescence determined. A 1:10 mixture of fluorescein isothiocyanate (FITC):phenyl isothiocyanate (PITC) in DMF was used as label in order to minimize fluorescence self quenching effects. The mount of amines generated from proteolysis of the different peptides was expected to reflect the relative $k_{cat}/K_m$ values of the peptides.

It was observed that two of the linkers, CAP and TRIGLY, gave very low signals. It appeared that complete proteolysis had not taken place and these two surfaces were excluded from further analysis. Of the remaining four linkers, the relative extent of proteolysis was determined as well as the relative rate of proteolysis. Extended incubation (4 hours to overnight) of the surface with a large amount of thermolysin (500 nM) established that complete proteolysis could take place with each of the three substrate peptides. The data for relative proteolysis rates (normalized to GFLAG as 100) is represented below:

TABLE 3

Proteolytic Rates for Peptides Attached to Solid Supports via Alternative Linking Group Combinations

| Linking Group | GGLAG | GALAG | GFLAG |
|---|---|---|---|
| 15-ATOM-PEG | 0.9 | 49 | 100 |
| 15-ATOM-PEG—15-ATOM-PEG | 1.5 | 54 | 100 |
| TRIGLY—TRIGLY | 7.2 | 60 | 100 |
| CAP—CAP | 5.0 | 73 | 100 |

It was observed that the proteolysis rates for GFLAG were relatively similar among all the different surfaces and that both the 15-ATOM-PEG and 15-ATOM-PEG-15-ATOM-PEG surfaces gave the maximum differentiation between the peptides examined. The TRIGLY—TRIGLY surface showed the highest level of background signal, indicative of a high level of non-specific binding. It was also noted that the observed relative proteolysis rates (GFLAG>GALAG>GGLAG) matched those measured in solution. From these observations it was concluded that the surfaces prepared with the 15-ATOM-PEG linker represented the optimum surface for conducting further proteolysis experiments.

Example 5

This example illustrates the synthesis of the photochemically cleavable linking group 4-(4-(1-(9-Fluorenylmethoxycarbonylamino)ethyl)-2-methoxy-5-nitrophenoxy)butanoic acid.

(a) Preparation of Methyl 4-((4-acetyl-2-methoxy) phenoxy)butanoate, 11.

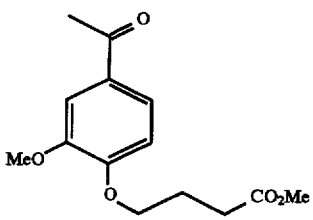

11

A slurry of acetovanillone (41.00 g, 246.7 mmol), methyl 4-bromobutyrate (50.15 g, 277 mmol), and $K_2CO_3$ (51.3 g, 371 mmol) in 200 mL of DMF was stirred at room temperature for 16 hours. Water was added to the reaction mixture until all the $K_2CO_3$ was dissolved and the solution was then partitioned between EtOAc and saturated NaCl. The organic phase was dried ($MgSO_4$), filtered and evaporated to dryness to afford 68.40 g (100% crude yield) of the product ketoester 11 as a light yellow oil, which slowly solidified, MP 48°–49° C.

(b) Preparation of Methyl 4-(4-(1-hydroxyiminoethyl-2-methoxy)phenoxy)butanoate, 12.

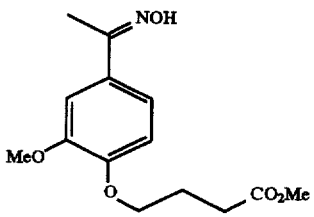

12

To a solution of the keto ester 11 from above (68.4 g) in 225 mL of 2:1 pyridine:$H_2O$ was added hydroxylamine hydrochloride (21.46 g, 309 mmol). After stirring at room temperature for 14 hours the reaction mixture was partitioned between EtOAc and saturated NaCl. The organic phase was dried ($MgSO_4$), filtered and evaporated to dryness to afford the oxime product 12 as a white solid (69.94 g, 100% crude yield), MP 82°–83° C.

(c) Preparation of Methyl 4-(4-(1-trifluoroacetamidoethyl-2-methoxy)phenoxy)butanoate, 13.

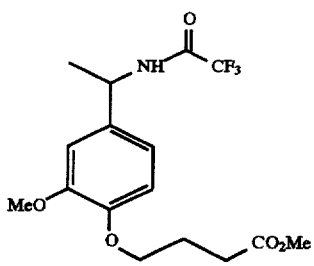

13

A slurry of the oxime 12 from above (69.9 g, 146.7 mmol theoretical) and palladium catalyst (2.5 g of 10% on charcoal, Lancaster Synthesis Inc.) in 400 mL of glacial acetic acid was degassed twice with a water aspirator and placed under 1.1 atmosphere of hydrogen gas via a balloon. An additional 2 g of catalyst was added after 18 h and the balloon was refilled with hydrogen as the gas was consumed. An additional 2 g of catalyst was added after 2 days. The reaction mixture was filtered after 5 days and the solvent was removed under vacuum. The oily residue was taken up in 600 mL of water and acidified to pH 1 with 6N HCl. The aqueous phase was washed with $Et_2O$, then basified with solid NaOH to pH 11 and extracted with EtOAc. The EtOAc extract was dried ($MgSO_4$), filtered and evaporated to dryness to afford a crude amine as a colorless oil.

The crude amine was dissolved in 300 mL of pyridine, cooled to 0° C. with an ice bath, and was treated with trifluoroacetic anhydride (31 mL, 219 mmol) for 1 hour before being partitioned between EtOAc and saturated NaCl. The organic phase was dried ($MgSO_4$), filtered and evaporated to dryness to give the crude trifluoroacetamide 13 as a light yellow solid. The solid was recrystallized from $CH_2Cl_2$/hexanes to afford 71.62 g of white solid (80% overall yield from acetovanillone), MP 96–97° C.

(d) Preparation of Methyl 4-(2-methoxy-5-nitro-4-(1-trifluoroacetamidoethyl)-phenoxy)butanoate, 14.

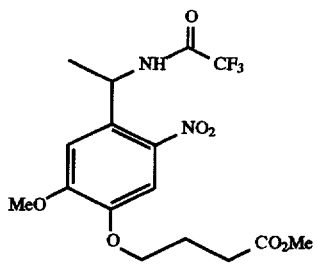

14

The trifluoroacetamide 13 from above (9.40 g, 25.9 mmol) was dissolved in 200 mL of 70% $HNO_3$ cooled to 0° C. The solution turned orange in color and was quenched after 2 hours by pouring into water and adjusting the total volume to 2 L. The resultant slurry was chilled to 4° C. overnight and filtered to give a light yellow solid. Recrystalization from MeOH/$H_2O$ afforded 9.07 g (86% yield) of product 14 as a light yellow solid, MP 156°–157° C.

(e) Preparation of 4-(4-(1=(9-Fluorenylmethoxycarbonylamino)ethyl)-2-methoxy5-nitrophenoxy)butanoic acid, 15.

15

To a solution of the nitro-phenyl compound 14 from above (12.36 g, 30.27 mmol) in 250 mL of warm MeOH was added 1N NaOH (100 mL, 100 mmol) and the reaction mixture was heated to reflux for 5 hours. The solution was cooled to room temperature and concentrated to about 100 mL with a rotary evaporator. Dioxane (150 mL) and $H_2O$ (100 mL) were added and the pH of the solution was adjusted to pH 9 with 6N HCl. A solution of FMOC-Cl (9.83 g, 38.0 mmol) in 100 mL of dioxane was added and an additional 15 mL of dioxane was added to create a homogeneous solution. The pH of the solution was measured to be 4.5 and was adjusted with 1N NaOH to pH 8 over the next 30 minutes. A light yellow precipitate formed as the pH was adjusted. The reaction was quenched after 18 h by adding 100 mL of 1N HCl and adjusting the total volume to 1 L with $H_2O$. The precipitate was collected, taken up in 1 L of hot EtOAc, dried over $MgSO_4$ and was filtered while hot. The solvent was removed under reduced pressure affording a light yellow solid which was triturated with 1 L of hot $Et_2O$. The solid was collected and was recrystallized from MeOH/10% hexanes to afford 12.78 g (81% yield for two steps) of product 15 as a light yellow solid, MP 200°–201 ° C.

Example 6

This example illustrates the photochemical cleavage of a series of linking groups.

Linking groups 1-6 were examined under photolysis conditions routinely employed for the synthesis of both peptides and oligonucleotides. Photolysis was carried out with a Hg(Xe) ARC lamp with a 350-450 nm dichroic reflector at an intensity of 10 mW/cm² at 365 nm. Roughly 90% of the UV light can be considered to be 365 nm in wavelength. The relative photolysis rates were measured in four different solvents (dioxane, methanol, pH 7.4 PBS, and pH 7.4 PBS containing 10 mM DTT). The substrate concentration was 0.1 mM and five time points were taken to determine the quantum yield and half-life for loss of starting material. The observed half-lives are shown in Table 4.

TABLE 4

Photolysis Half-Lives for Linkers 1-6

| Linking Group | Solvent | | | |
|---|---|---|---|---|
| | PBS | DTT/PBS | MeOH | Dioxane |
| 1 | 348 | 259 | a | a |
| 2 | 14.1 | 47.2 | 362 | 36.8 |
| 3 | 12.9 | 7.32 | 16.2 | 4.00 |
| 4 | 1.74 | 1.98 | 5.81 | 0.64 |
| 5 | 2.87 | 2.86 | 3.85 | 0.50 |
| 6 | 0.69 | 0.66 | 0.51 | 0.17 | a No photolysis observed.

As the results in Table 4 indicate, linking groups 3-6 show acceptable rates of photolysis in typical aqueous buffers. Additionally, linking groups 3 and 4 were examined for stability to TFA treatment which is used in some methods of solid phase polymer synthesis (i.e., a "Merrifield"-type peptide synthesis, FMOC-based peptide synthesis and spotting and flow channel methods associated with VLSIPS™). Linking groups 3 and 4 were each dissolved in both 50% TFA/CH₂Cl₂ and 95% TFA/H₂O for one hour. No decomposition of either linking group was observed by HPLC.

Example 7

This example illustrates the synthesis of thiazolidinones on a resin having a photocleavable linker and the subsequent removal of the thiazolidinones from the resin via photolysis.

Commercially available H₂N-S-TentaGel (Rapp Polymere, Tübingen, Germany, 1 g, 0.30 mmol/g loading) was washed with DMF and treated with 3 mL of a 0.2M solution of OBt-activated FMOC-photolinker (prepared from 310 mg of FMOC-linker, 92 mg of HOBt, 95 µL of DIC in 3 mL of DMF) for 1.5 hour. Ninhydrin test indicated a complete reaction had taken place. The resin was washed with DMF and CH₂Cl₂, and was then capped by treatment with 20 % Ac₂O and 30% pyridine in 50% CH₂Cl₂ for 30 minutes. The resin was washed (3×5 mL DMF, 3×5 mL CH₂Cl₂), and dried under vacuum for 1 hour. A portion of the resin (200 mg) was deprotected with 30 % piperidine/DMF for 30 minutes and then washed with DMF. A 0.5M solution of FMOC-Glycine symmetrical anhydride (prepared from 182 mg of FMOC-Gly-OH and 50/µL of DIC in 0.6 mL of DMF) was coupled to the resin for 1 hour, by which time ninhydrin had revealed that a complete reaction had taken place. The resin was washed and capped as above for 30 minutes. Deprotection with piperidine, washing and drying as above gave roughly 150 mg of dry resin. The dried resin was partitioned. (roughly 40 mg of resin per vial) into 2 4-mL vials equipped with a screw top closure. Acetonitrile (2 mL) and 3 Å molecular sieves (20-30 pellets) were added to each vial. Benzaldehyde (152 µL) and mercaptoacetic acid (300 µL) was added to the first vial whereas 2,4-dimethoxybenzaldehyde (250 mg) and mercaptoacetic acid (300 µL) was added to the second vial. Both vials were heated to 70° C. for 2 hours. The vials were cooled to room temperature and the resin was transferred to disposable filter tubes and washed extensively (3×5 mL CH₂Cl₂, 3×5 mL DMF, 3×5 mL CH₂Cl₂, 3×5 mL MEOH, 3×5 CH₂Cl₂, 3×5 mL Et₂O). Roughly 2 mg of each of the two types of resin were placed in plastic centrifuge tubes equipped with 0.22 µm membrane filters (Ultrafree-MC Filter Units from Millipore, Bedford, Mass.) and were suspended in 100 µL of pH 7.4 PBS buffer. Photolysis were conducted with a 500 W Hg ARC lamp fitted with a 350-450 nm dichroic mirror at a 10 mW/cm² power level measured at 365 nm. The samples were irradiated from above for various times and the samples were gently mixed during photolysis with an orbital shaker table. After photolysis the samples centrifuged and the flitrate collected. The samples were washed with 100 µL of 50% CH₃CN/H₂O and again centrifuged. The collected filtrates from each sample were analyzed by HPLC for the presence of thiazolidinone. See FIG. 2. The data indicated that both the thiazolidinones were produced in high purity on the resin and that they were stable to the photolysis conditions.

VII. Conclusion

The above description is illustrative and not restrictive. Many variations of the invention will become apparent to those of skill in the art upon review of this disclosure. Merely by way of example a variety of substrates, receptors, ligands, and other materials may be used without departing from the scope of the invention. The scope of the invention should, therefore, be determined not with reference to the above description, but instead should be determined with reference to the appended claims along with their full scope of equivalents.

What is claimed is:

1. A composition having the formula:

wherein A is a solid substrate,

B is a bond or a derivatizing group selected from the group consisting of aminoalkyltrialkoxysilanes, hydroxylalkyltrialkoxysilanes, polyethyeleneglycols, polyethyleneimines, polyacrylamide, and polyvinylalcohol; and L is a photocleavable linking group having the formula

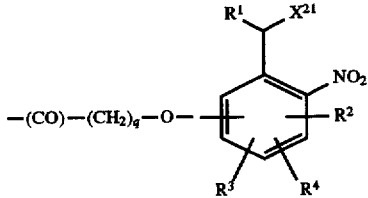

wherein, $R^1$ is methyl;

$R^3$ is methoxy;

$R^2$ and $R^4$ are hydrogen;

$X^{21}$ is —OH, —NH₂, —OP, and —NHP, wherein P is a suitable protecting group; and q is 1 or 3.

2. A composition in accordance with claim 1, wherein L has the formula:

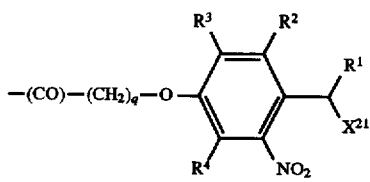

wherein
R$^1$ is methyl;
R$^3$ is methoxy;
R$^2$ and R$^4$ are hydrogen;
X$^{21}$ is —OH, —OP, —NH$_2$, and —NHP, wherein P is a suitable protecting group; and
q is 3.

3. A composition in accordance with claim 1, wherein L has the formula:

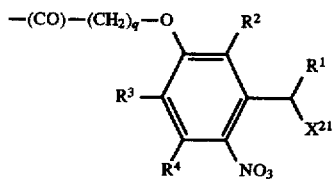

wherein
R$^1$ is methyl;
R$^2$ and R$^4$ are hydrogen;
R$^3$ is methoxy;
X$^{21}$ is —OH, —OP, —NH$_2$, and —NHP, wherein P is a suitable protecting group; and
q is3.

4. A composition in accordance with claim 2 or 3, wherein X$^{21}$ is —OH.

5. A composition in accordance with claim 2 or 3, wherein X$^{21}$ is —NH$_2$.

6. A composition in accordance with claim 2 or 3, wherein X$^{21}$ is —NHP and P is Fmoc.

7. A composition comprising a plurality of beads wherein each of said beads further comprises a linker having the formula

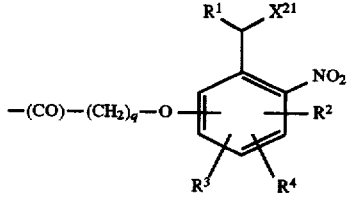

wherein,

R$^1$ is methyl;
R$^3$ is methoxy;
R$^2$ and R$^4$ are hydrogen
X$^{21}$ is —OH, —NH$_2$, —OP, and —NHP, wherein P is a suitable protecting group; and
q is 1 or 3.

8. The composition of claim 7 wherein said linker has the formula:

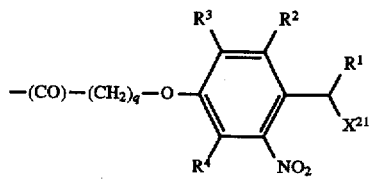

wherein,

R$^1$ is methyl;
R$^3$ is methoxy;
R$^2$ and R$^4$ are hydrogen;
X$^{21}$ is —OH, —NH$_2$, —OP, and —NHP, wherein P is a suitable protecting group; and
q is 3.

9. The composition of claim 7, wherein said linker has the formula:

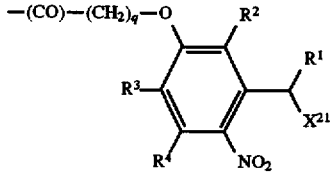

wherein,

R$^1$ is methyl;
R$^3$ is methoxy;
R$^2$ and R$^4$ are hydrogen;
X$^{21}$ is —OH, —NH$_2$, —OP, and —NHP, wherein P is a suitable protecting group; and
q is3.

10. The composition of claim 6 or 7, wherein X$^{21}$ is —OH.

11. The composition of claim 6, wherein X$^{21}$ is —NHP and P is Fmoc.

* * * * *